United States Patent [19]

Hiemstra-Paez

[11] Patent Number: 5,067,484
[45] Date of Patent: Nov. 26, 1991

[54] POSTURE TRAINING SUPPORT WITH WEIGHT POCKETS

[75] Inventor: Carol L. Hiemstra-Paez, Spring Arbor, Mich.

[73] Assignee: Camp International, Inc., Jackson, Mich.

[21] Appl. No.: 578,739

[22] Filed: Sep. 6, 1990

[51] Int. Cl.⁵ .......................... A61F 5/02; A63B 21/00
[52] U.S. Cl. ...................................... 128/78; 272/119
[58] Field of Search ................ 128/846, 78, 100, 95, 128/99, 68, 69, 96.1, 102, 875, 876; 272/119, 143

[56] References Cited

U.S. PATENT DOCUMENTS

| | | | |
|---|---|---|---|
| 3,374,636 | 3/1968 | Mason | 272/119 |
| 3,532,339 | 10/1970 | Smith | 272/119 |
| 3,588,105 | 6/1971 | Donohoe | 272/119 |
| 3,735,598 | 5/1973 | Oeland | 272/119 |
| 3,888,245 | 6/1975 | Berntson | 272/119 |
| 3,924,851 | 12/1975 | Winston | 272/119 |
| 4,099,524 | 7/1978 | Cueman | 128/78 |
| 4,180,261 | 12/1979 | Kolka | 272/119 |
| 4,303,239 | 12/1981 | Walsh, Jr. | 272/119 |
| 4,552,135 | 11/1985 | Racz | 128/78 |
| 4,768,499 | 9/1988 | Kemp | 128/78 |

Primary Examiner—Robert A. Hafer
Assistant Examiner—Michael Brown
Attorney, Agent, or Firm—Price, Heneveld, Cooper, DeWitt & Litton

[57] ABSTRACT

The specification discloses a method and support for posture training. The support comprises a soft, cushiony pouch for holding one or more weights within pockets located in the pouch. The pouch is positionable on the back of a patient below the inferior angle of the patient's scapulae by adjustable clavicle straps secured to the pouch.

38 Claims, 1 Drawing Sheet

5,067,484

POSTURE TRAINING SUPPORT WITH WEIGHT POCKETS

CROSS REFERENCE TO RELATED APPLICATION

This invention is an improvement on the invention claimed in U.S. Pat. application Ser. No. 07/579,349, entitled "POSTURE TRAINING SUPPORT" filed on even date herewith.

BACKGROUND OF THE INVENTION

The present invention relates to posture training. The words "posture training" as used herein are intended to be given a broad interpretation, to encompass, for example, "posture control."

A variety of circumstances can lead to the deterioration of a person's posture. One such circumstance is disease such as osteoporosis or neurological disease. Work or study positions, such as bending over a computer, a work table, a desk or a machine, for example, can lead to deteriorated posture in children and adults. Pregnant women, women with heavy anatomy at the anterior chest or women with balance problems due to kyphosis can develop poor posture.

Present treatment for such posture disorder focuses on the use of restraints to hold a desired posture position. Such restraints include thoracolumbar supports and shoulder orthoses. The thoracolumbar support is basically a corset device. The shoulder orthoses are devices which use a back brace in combination with a thoracic band and clavicle straps to hold the preferred posture position. However, the rigid restraint of these devices does not encourage the wearer to actively use his or her muscles to achieve good posture Further, because at least a portion of such devices wrap around the thoracic cavity and/or abdomen, they are uncomfortable for the patient. In treating osteoporosis, such devices which incorporate a rigid member can cause further damage to the frail skeletal structure. The restraining clavicle straps of the thoracolumbar supports are also uncomfortable. The discomfort aspect of such devices diminishes their effectiveness as the patient will avoid using an uncomfortable device.

SUMMARY OF THE INVENTION

The posture training support of the present invention presents a unique approach to posture training treatment by using a small pouch to position a weight on the back of the patient, below the inferior angle of the patient's scapulae. The pouch is held in place by adjustable clavicle straps and can be worn under the patient's clothing.

The support of the present invention does not use the restraint approach of the prior art. The invention uses a biomechanical approach to appropriately position a weight to counteract the patient's tendency to stoop forward and allows the design of a significantly more comfortable support which in turn is more likely to be used by the patient.

These and other objects, advantages and features of the present invention will become apparent upon review of the following specification in conjunction with the drawings.

DESCRIPTION OF THE PREFERRED EMBODIMENT

Figure 1:
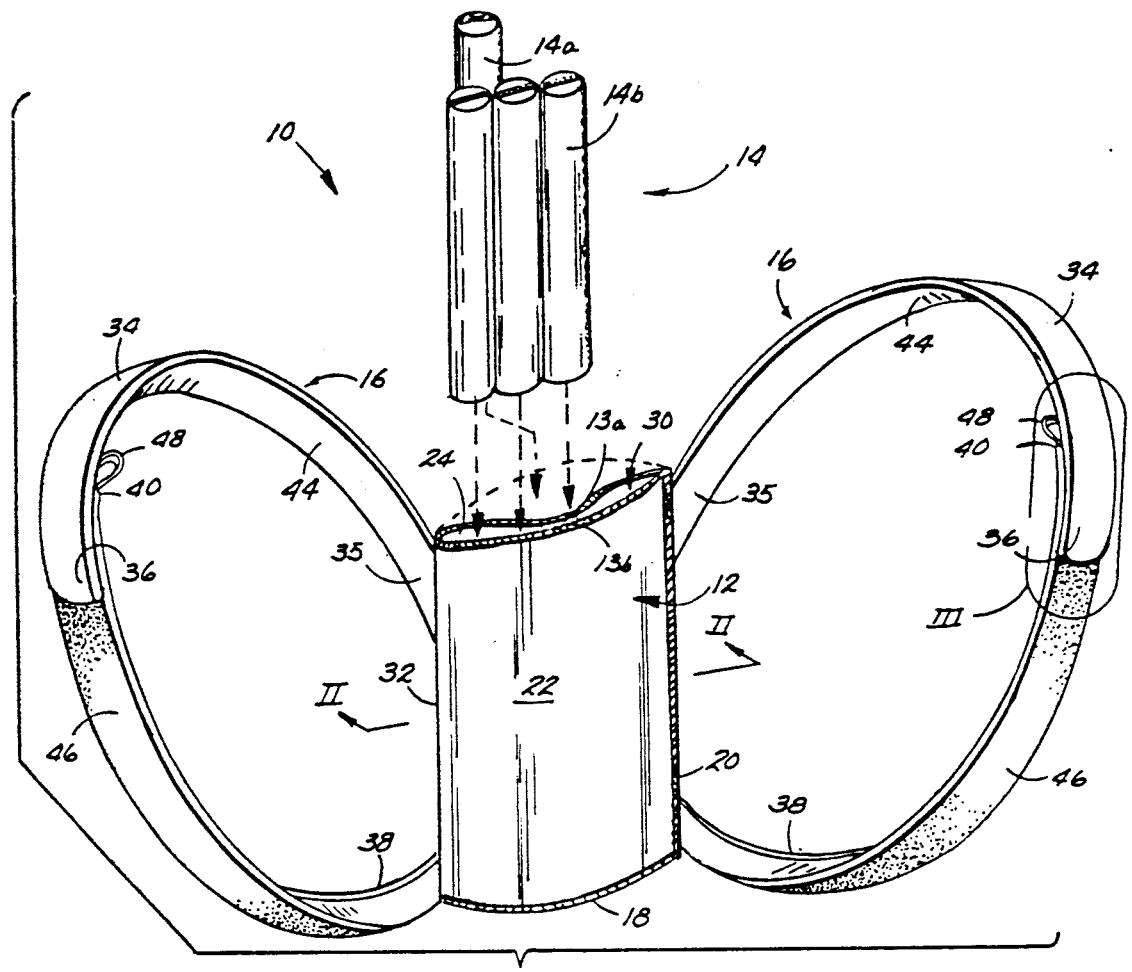
FIG. 1 is a frontal perspective view of the support of the present invention and shows the method of adding weight to the invention with the pouch shown in the open position in phantom.

In the preferred embodiment, the posture training support 10 of the present invention has a pouch 12 for holding weights 14 and clavicle straps 16 for securing the pouch 12 and weights 14 to the back of a patient (FIG. 1).

Pouch 12 is preferably made of a single piece of soft, durable material, such as a relatively thick, spongy material, with a loop pile surface to give a soft feel. The material is folded over itself and sewn along two sides 18 and 20 to form the rectangular pouch 12 with open top 30 (FIG. 1).

Figure 2:
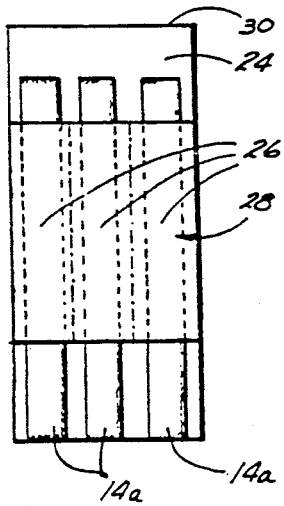
FIG. 2 is a sectional view of the pouch as indicated by section line II—II in FIG. 1.

Pouch 12 has a front portion 22 which lays against the back of a patient in use and a back portion 24 which faces away from the patient in use. Weight pockets 26 are provided on the inside surface of back portion 24 for holding individual weights 14a (FIG. 2). Weight pockets 26 are formed by sewing a band of elastic material 28 to the inside surface of back portion 24 so that equal loops are formed in the elastic material 28 to define the weight pockets 26.

Pouch 12 is small and thin so as to be unobtrusive when worn. Its length and width define an area which is preferably significantly smaller than the area of a median adult back, indeed preferably less than one-half such back area and most preferably less than one-quarter such back area. On a larger back, pouch 12 nestles into the space between the lower portions of the shoulder blades. Pouch 12 is from about 4 to 8 inches long, about 2 to 4 inches wide, and no thicker than about 0.5 inch when empty and about 1.5 inches when filled with weights 14. A most preferred length is about 7 inches and a most preferred width is about 3.5 inches. Pouch 12 preferably has some thickness when empty in that pouch 12 is preferably made of a soft cushiony material for comfort.

Pouch 12 includes a hook 13a and loop 13b closure system at open top 30 so that weights 14 which are placed in pouch 12 do not bounce out or otherwise work their way out of pouch 12 when walking vigorously or running.

Individual weights 14a are secured in pockets 26 (FIG. 2). The large, multiple weight 14b does not need to be secured in pockets 26. When weight 14b is used, it is simply placed inside pouch 12 (FIG. 1). Each weight 14 is preferably a relatively soft, pliable weight, such as can be made by filling a fabric pocket with metallic pellets, so that the weights 14 will conform to the surface of the patient's back to enhance comfort. Further, when individual weights 14a are used in combination with the multiple weight 14b, the multiple weight 14b is preferably positioned near the patient's back and the individual weights 14a positioned away from the patient's back for enhanced comfort.

Each individual weight 14a weighs approximately 4 ounces. Multiple weight 14b preferably weighs about 16 ounces. Thus, the weight is adjustable in 0.25 pound increments to a total of about 1.75. Obviously, some variation in these weights is permissible within the broader aspects of the invention. You could, for example, simply use two 1-pound weights in pouch 12.

Figure 3:
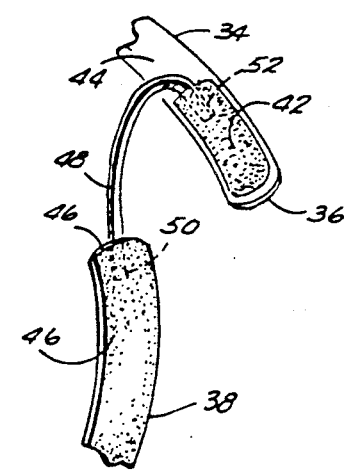
FIG. 3 is a detailed view of the strap adjustment means as indicated by detail III in FIG. 1.

Clavicle straps 16 are attached to pouch 12 near the top 30 and the bottom 18 of each side 20 and 32 (FIG. 1). Each strap 16 has an upper portion 34 which has an end 36, away from pouch 12, and a lower portion 38 which has an end 40, away from pouch 12. A patch 42 of the hook portion of a hook and loop fastening fabric is attached to the inner surface 44 at end 36 of each upper portion 34 (FIG. 3). The outer surface 46 of each lower portion 38 is provided with a loop pile material for fastening engagement with hook patch 42. An elastic tether 48 is fastened on each strap 16. Each tether 48 has a first end 52 fastened to each upper portion 34 near the edge of hook patch 42 away from end 36 (FIG. 3). The second end 50 of tether 48 is attached at the end 40 of each lower portion 38. In the preferred embodiment, tether 48 is approximately 4 inches long and stretches to approximately 9 inches.

The pouch 12 is properly positioned preferably just below the inferior angle of the scapulae on the back of the patient. Such proper positioning is accommodated in a range of patient sizes by the adjustability of straps 16. The use of hook patch 42 and the loop pile material on the outer surface 46 of each lower portion 38 provides a comfortable adjustment range for each strap of approximately 6 inches. Further, a range of sizes of straps is provided, such as double extra small, with lengths of approximately 9.75 inches and 13.75 inches for the upper and lower portions 34 and 38 respectively, through extra large, with lengths of approximately 13.75 inches and 17.75 inches for the upper and lower portions 34 and 38 respectively. Thus, support 10 can be used for a large range of patient sizes with some variation permissible within the broader aspects of the invention.

In use, a combination of weights 14 is selected by the treating physician for the appropriate amount of weight to treat a specific patient. Individual weights 14a are secured in weight pockets 26 of pouch 12 (FIG. 2). A multiple weight 14b is simply placed inside pouch 12 and does not need to be secured in weight pockets 26 (FIG. 1).

The patient wears support 10, under his or her clothing, by inserting his or her arms through clavicle straps 16 with ends 36 and 40 separated. Elastic tethers 48 keep ends 36 and 40 in proximity to each other and thereby make it easier to fasten ends 36 and 40 of straps 16, once straps 16 are in place over the patients arms. The fact that tethers 48 are elastic, makes it easier for the patient to position and fasten the straps 16. Pouch 12, containing weights 14, is positioned below the inferior angle of the patient's scapulae and the clavicle straps 16 are adjusted for the patient's comfort to secure pouch 12 in the proper position. This adjustment is easily accomplished by varying the point at which hook patch 42 is lapped over the loop pile of surface 46.

The above description is considered that of the preferred embodiment only. Modifications of the invention will occur to those who make or use the invention. Therefore, it is understood that the embodiments shown in the drawings and described above is merely for illustrative purposes and is not intended to limit the scope of the invention, which is defined by the following claims as interpreted according to the principles of patent law.

The embodiments of the invention in which an exclusive property or privilege is claimed are defined as follows:

1. A posture training support comprising:
    a pouch for holding weight on the back of a patient, said pouch having length, width and thickness, said length and width defining an area which is significantly smaller than the area of the back of a median adult patient, said thickness being sufficiently thin so that said pouch can be unobtrusively worn under the patient'clothing;
    means dividing the interior of said pouch into at least two separate pockets, each for holding a weight against excessive movement within said pocket and within said pouch;
    at least one weight smaller in dimension than the interior dimensions of said pouch and comparable in dimensions to at least one of said pockets whereby said weight is snugly located in one of said pockets in said pouch; and
    clavicle straps secured to said pouch for strapping said pouch onto a patient's back.

2. The support defined in claim 1 wherein said pouch includes an open top whereby said weight can be removed from said pouch and additional weights can be added.

3. The pouch of claim 2 which includes four of said pockets within said pouch;
    three of said pockets being relatively small for receiving relatively small weights, and one of said pockets being relatively large for receiving a larger weight.

4. The posture training support of claim 3 which includes at least two of said weights, each having a configuration corresponding to the shape of said small pockets such that each of said weights is fitted snugly in one of said small pockets.

5. The posture training support of claim 4 which comprises three of said small weights, each fitted into one of said three small pockets.

6. The posture training support of claim 5 which additionally includes one larger weight configured such that it fits snugly into said large pocket of said pouch.

7. The posture training support of claim 6 in which each said weight is of a relatively soft, pliable construction such that it tends to feel more comfortable on a patient's back.

8. The posture training support of claim 7 in which said pouch is made of a soft, cushiony fabric such that it feels soft against the user's back.

9. The support defined in claim 8 wherein said straps are sized to position said pouch below the inferior angle of the patient's scapulae.

10. The support defined in claim 9 in which said open top of said pouch includes closure means whereby said weight is held in place within said pouch 11. The support defined in claim 10 in which said pouch is smaller in area than one-half the area of a median adult back.

12. The support defined in claim 11 in which said pouch is smaller in area than one-quarter the area of a median adult back.

13. The support defined in claim 12 in which said pouch is about seven inches long by about three and one-half inches wide.

14. The support defined in claim 13 in which said pouch is no thicker than about one and one-half inches when filled with said weights.

15. The support defined in claim 3 wherein said straps are sized to position said pouch below the inferior angle of the patient's scapulae.

16. The support defined in claim 15 in which said open top of said pouch includes closure means whereby said weight is held in place within said pouch.

17. The posture training support of claim 16 in which each said weight is of a relatively soft, pliable construction such that it tends to feel more comfortable on a patient's back.

18. The posture training support of claim 17 in which said pouch is made of a soft, cushiony fabric such that it feels soft against the user's back.

19. The support of claim 3 in which said weight is larger weight configured such that it fits snugly into said large pocket of said pouch.

20. The pouch of claim 2 which includes four of said pockets within said pouch;
three of said pockets being relatively small for receiving relatively small weights, and one of said pockets being relatively large for receiving a larger weight.

21. The posture training support of claim 20 in which each said weight is of a relatively soft, pliable construction such that it tends to feel more comfortable on a patient's back.

22. The posture training support of claim 21 in which said pouch is made of a soft, cushiony fabric such that it feels soft against the user's back.

23. The posture training support of claim 20 in which said pouch is made of a soft, cushiony fabric such that it feels soft against the user's back.

24. The support defined in claim 1 wherein said straps are sized to position said pouch below the inferior angle of the patient's scapulae.

25. The posture training support of claim 24 in which each said weight is of a relatively soft, pliable construction such that it tends to feel more comfortable on a patient's back.

26. The posture training support of claim 25 in which said pouch is made of a soft, cushiony fabric such that it feels soft against the user's back.

27. The posture training support of claim 24 in which said pouch is made of a soft, cushiony fabric such that it feels soft against the user's back.

28. The posture training support of claim 1 in which each said weight is of a relatively soft, pliable construction such that it tends to feel more comfortable on a patient's back.

29. The posture support of claim 28 in which said pouch is made of a soft, cushiony fabric such that it feels soft against the user's back.

30. The posture training support of claim 1 in which said pouch is made of a soft, cushiony fabric such that it feels soft against the user's back.

31. A method for posture training comprising:
positioning a pouch on the back of a patient, said pouch having length and width defining an area which is significantly smaller than the area of a median adult patient's back, said pouch having thickness which is sufficiently thin so that said pouch can be unobtrusively worn under the patient's clothing, said pouch having at least two pockets, each for receiving a separate weight, defined within said pouch;
securing said pouch to the patient with clavicle straps which are secured to the pouch;
providing a plurality of individual weights for placing in said pouch whereby the amount of weight in said pouch can be adjusted by the number of weights used, each weight being smaller in dimensions that the interior of said pouch whereby all of said plurality of weights can be fitted into said pouch, but each said weight being comparable in dimensions to one of said pockets whereby it fits snugly into one of said pockets;
snugly locating at least one of said weights in at least one of said pockets to thereby shift the user's center of gravity and facilitate posture training.

32. The method defined in claim 31 further including locating the pouch below the inferior angle of the patient's scapulae.

33. The method defined in claim 32 wherein the pouch is provided with an open top whereby weight is added to and removed from the pouch and provided with a closure for closing the top and holding weight within the pouch.

34. The method defined in claim 33 wherein:
three small pockets are provided within said pouch, each for receiving one small weight;
wherein one large pocket is provided within said pouch for receiving one large weight; and
wherein said step of providing said plurality of individual weights comprises providing three small weights, each configured for being received and held by one of said small pockets, and one large weight, configured to be received and held in said large pocket.

35. The method defined in claim 34 further including constructing each weight to be relatively soft and pliable so that it tends to conform to the user and enhance the patient's comfort.

36. The method of claim 35 further including fabricating said pouch from a soft, cushiony fabric to enhance the patient's comfort.

37. The method defined in claim 31 wherein:
three small pockets are provided within said pouch, each for receiving one small weight;
wherein one large pocket is provided within said pouch for receiving one large weight; and
wherein said stp of providing said plurality of individual wights comprises providing three small weights, each configured for being received and held by one of said small pockets, and one large weight, configured to be received and held in said large pocket.

38. The method defined in claim 31 further including constructing each weight to be relatively soft and pliable so that is tends to conform to the user and enhance the patient's comfort.

* * * * *

UNITED STATES PATENT AND TRADEMARK OFFICE
CERTIFICATE OF CORRECTION

PATENT NO. : 5,067,484
DATED : November 26, 1991
INVENTOR(S) : Carol L. Hiemstra-Paez It is certified that error appears in the above-identified patent and that said Letters Patent is hereby corrected as shown below:

Column 2, line 24:
  "cf back" should be --of back--.

Column 5, line 11:
  After "is" please insert
  therefor --a--.

Column 5, line 47:
  After "posture" please insert
  therefor --training--.

Column 6, line 41, claim 36:
  "of claim" should be
  --defined in claim--.

Column 6, line 49, claim 37:
  "stp" should be --step--.

Column 6, line 50, claim 37:
  "wights" should be --weights--.

Signed and Sealed this

Eighth Day of June, 1993

Attest:

MICHAEL K. KIRK

Attesting Officer

Acting Commissioner of Patents and Trademarks